(12) United States Patent
Baszczynski et al.

(10) Patent No.: US 7,179,599 B2
(45) Date of Patent: *Feb. 20, 2007

(54) MOBILIZATION OF VIRAL GENOMES FROM T-DNA USING SITE-SPECIFIC RECOMBINATION SYSTEMS

(75) Inventors: Christopher L. Baszczynski, Urbandale, IA (US); Leszek Alexander Lyznik, Johnston, IA (US); William J. Gordon-Kamm, Urbandale, IA (US); Xueni Guan, San Diego, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 220 days.

This patent is subject to a terminal disclaimer.

(21) Appl. No.: 10/444,664

(22) Filed: May 23, 2003

(65) Prior Publication Data

US 2004/0005713 A1  Jan. 8, 2004

Related U.S. Application Data

(60) Continuation of application No. 09/411,826, filed on Oct. 1, 1999, now Pat. No. 6,664,108, which is a division of application No. 09/193,475, filed on Nov. 17, 1998, now Pat. No. 6,300,545.

(60) Provisional application No. 60/099,461, filed on Sep. 8, 1998, provisional application No. 60/065,627, filed on Nov. 18, 1997, and provisional application No. 60/065,613, filed on Nov. 18, 1997.

(51) Int. Cl.
*C12Q 1/68* (2006.01)
*C12N 1/12* (2006.01)
*C12N 1/20* (2006.01)
*C12N 15/00* (2006.01)
*C12N 15/09* (2006.01)

(52) U.S. Cl. .................. 435/6; 435/325; 435/320.1; 435/252.3; 435/410

(58) Field of Classification Search .............. 435/6, 435/325, 320.1, 252.3, 410
See application file for complete search history.

(56) References Cited

U.S. PATENT DOCUMENTS

| | | | |
|---|---|---|---|
| 5,677,177 A | 10/1997 | Wahl et al. | |
| 5,744,336 A | 4/1998 | Hodges et al. | |
| 6,010,884 A | 1/2000 | Griffiths et al. | |
| 6,171,861 B1 | 1/2001 | Hartley et al. | |
| 6,187,994 B1 | 2/2001 | Baszczynski et al. | |
| 6,262,341 B1 | 7/2001 | Baszczynski et al. | |
| 6,300,545 B1 * | 10/2001 | Baszczynski et al. ....... | 800/294 |
| 6,331,661 B1 | 12/2001 | Baszczynski et al. | |
| 6,455,315 B1 | 9/2002 | Baszczynski et al. | |
| 6,458,594 B1 | 10/2002 | Baszczynski et al. | |
| 6,541,231 B1 | 4/2003 | Baszczynski et al. | |
| 6,552,248 B1 | 4/2003 | Baszczynski et al. | |
| 6,573,425 B1 | 6/2003 | Baszczynski et al. | |
| 6,624,297 B1 | 9/2003 | Baszczynski et al. | |
| 6,774,279 B2 | 8/2004 | Dymecki | |
| 2003/0119166 A1 | 6/2003 | Basczynski et al. | |

FOREIGN PATENT DOCUMENTS

| | | |
|---|---|---|
| GB | 2 174 995 A | 11/1986 |
| WO | WO 92/15694 | 9/1992 |
| WO | WO 93/01283 | 1/1993 |
| WO | WO 93/17116 | 9/1993 |
| WO | WO 94/17176 | 8/1994 |
| WO | WO 95/00555 | 1/1995 |
| WO | WO 95/15388 | 6/1995 |
| WO | WO 96/04393 | 2/1996 |
| WO | WO 97/09436 | 3/1997 |
| WO | WO 97/09439 | 3/1997 |
| WO | WO 97/13401 | 4/1997 |
| WO | WO 97/37012 | 10/1997 |
| WO | WO 97/47758 | 12/1997 |
| WO | WO 99/23202 | 5/1999 |
| WO | WO 99/55851 | 11/1999 |

OTHER PUBLICATIONS

Abremski, K.E., and R. Hoess, "Evidence for a Second Conserved Arginine Residue in the Integrase Family of Recombination Proteins," *Protein Engineering*, 1992, pp. 87–91, vol. 5(1), Oxford University Press.

(Continued)

*Primary Examiner*—James Ketter
*Assistant Examiner*—Konstantina Katcheves
(74) *Attorney, Agent, or Firm*—Alston & Bird LLP

(57) ABSTRACT

The invention relates to methods and compositions for site-specific recombinase-mediated mobilization of viral replicons and associated DNAs of interest from T-DNA. The methods of the invention comprise *Agrobacterium*-mediated transfer of T-DNA to a plant cell, wherein the T-DNA contains a viral replicon flanked by directly repeated target sites for a site-specific recombinase and optionally a DNA of interest linked to the viral replicon. The DNA of interest may also contain a non-identical target site for the recombinase. An expression cassette for the site-specific recombinase is present on the T-DNA or the plant genome, or is transiently introduced into the plant cell. Expression of the site-specific recombinase in the plant cell results in excision of the viral replicon and the associated DNA of interest. The viral replicon and DNA of interest are then replicated to high copy number in the host plant cell. The compositions of the invention comprise nucleic acids, such as T-DNAs containing a viral DNA flanked by directly repeated target sites for a site-specific recombinase. The nucleic acids of the invention may additionally contain expression cassettes encoding the cognate site-specific recombinase for the target sites flanking the viral genome. The compositions of the invention further comprise *Agrobacterium* containing the nucleic acids of the invention. The compositions and methods of the invention have use in increasing the efficiency of agroinfection, providing high copy numbers of a DNA of interest for transient expression or for integration into a plant chromosome, and in simplifying the construction and stable maintenance of vectors for agroinfection and transformation.

62 Claims, 5 Drawing Sheets

OTHER PUBLICATIONS

Albert et al., Site–Specific Integration of DNA into Wild–Type and Mutant Lox Sites Placed in the Plant Genome, *The Plant Journal* .(Jan. 18, 1995) pp. 649–659 vol. 7, No. 4, Plant Gene Expression Center, USDA/ARS–UC Berkeley, Albany, CA.

Araki et al,. "Targeted Integration of DNA Using Mutant Lox Sites in Embryonic Stem Cells," *Nucleic Acids Research* (1997) pp. 868–872 vol. 25(4) Dept. Dev. Genetics, Institute of Molecular Embryology and Genetics, Kumamoto University, Kumamoto Japan & Gene Tech. Center, Kumanoto, Japan.

Bethke et al., "Segmental Genomic Replacement by Crer–Mediated Recombination: Genotoxic Stress Activation of the P53 Promoter in Single–Copy Transformants," *Nucleic Acids Research* (1997) pp. 2828–2834 vol. 25(14) National Institutes of Health, National Institute of Diabetes, Digestive and Kidney Disease, Bethesda, MD.

Campbell et al., Codon Usage in Higher Plants, Green Algae, and Cyanobacteria, Plant Physiol., 1990, pp. 1–11, vol. 92, Houghton, Michigan.

Czako et al. (1997) "Negative Selection Markers for Plants", Technology Transfer of Plant Biotechnology, Chapter 6, CRC Press, Inc., Edited by Peter M. Gresshoff, Plant Molecular Genetics, Institute of Agriculture, Center for Legume Research, The University of Tennessee, Knoxville, Tennessee, pp. 67–93.

Dale et al., Gene Transfer with Susequent Removal of the Selection Gene from the Host Genome, Proc. Natl. Acad. Sci. USA (Dec. 1991) pp. 10558–10562, vol. 88: Plant Gene Expression Center, USDOA/Agr. Res. Svs., Albany, CA and Dept. Plant Pathology, Univ. of Calif, Berkeley, California.

Dasgupta et al. (1991) "Rice Tungro Bacilliform Virus DNA Independently Infects Rice After *Agrobacterium*–Mediated Transfer", *Journal of General Virology* 72:1215–1221.

Feil et al., "Regulation of Cre Recombinase Activity by Mutated Estrogen Receptor Ligand–Binding Domaiins," *Biochem. and BioPhy. Res. Comm* (1997) pp. 172–757, vol. 237 Institute de Genetique et de Biologie Moleculaire et Cellulaire, College de France, Strasbourg, France.

Golic et al., FLP–Mediated DNA Mobilization to Specific Targets sites in *Drosophilia* Chromosomes, *Nucleic Acids Research* (1997) pp. 3665–3671 vol. 25(18) Dept. of Biol., Univ. of Utal, Salt Lake City, UT, Inst. Of Path., Case Western Res. Univ., Cleveland, OH, Howard Hughes Med. Inst., Univ. of Chicago, Chicago, IL.

Grimsley et al. (1988) "Meristematic Tissues of Maize Plants are Most Susceptible to Agroinfection with Maize Streak Virus", *Bio/Technology* 6:185–189.

Karreman et al. (1996) "On the Use of Double FLP Recognition Targets (FRTs) in the LTR of Retroviruses for the Construction of High Producer Cell Lines", *Nucleic Acids Research* 24(9):1616–1624.

Kilby et al., FLP Recombinase in Transgenic Plants: Constitutive Activity in Stably Transformed Tobacco and Generation of Marked Cell Clones in *Arabidopsis, The Plant Journal* (1995) pp. 637–652 vol. 8(5) Institute of Biotech., Univ. of Cambridge, Cambridge, UK.

Logie et al., Ligand–Regulated Site–Specific Recombination, *Proc. Natl. Acad. Sci. USA* (Jun. 1995) pp. 5940–5944 vol. 92 Gene Expression Program, Eur. Mol. Biol. Lab., Heidelberg, Germany.

Louie (1995) "Vascular Puncture of Maize Kernels for the Mechanical Transmission of Maize White Line Mosaic Virus and Other Viruses of Maize", *Phytopathological* 85(2);139–143.

Lyznik et al., Activity of Yeast FLP Recombinase in Maize and Rice Protoplasts, *Nucleic Acids Research*, 1993, pp. 969–975, vol. 21 No. 4, Oxford University Press.

Lyznik et al. *Heat—Inducible Expression of FLP Gene in Maize Cells* The Plant Journal (1995) pp. 177–186, vol. 8(2) Dept. of Botany and Plant Path. Purdue Univ. West Lafayette, IN.

Lyznik et al., FLP–Mediated Recombination of FRT Sites in the Maize Genome, Nucleic Acids Research, 1996, pp. 3784–3789, vol. 24, No. 19, Oxford University Press.

McLeod et al. Identification of the Crossover Site During FLP–Mediated Recombination in the *Saccharomyces Cerevisiae* Plasmid 2μm Circle, *Mol. Cell. Biol.,* Oct. 1986, pp 3357–3367, vol. 6(10), American Society for Microbiology, Cold Spring Harbor, New York.

Narasimhulu et al., Early Transcription of Agrobacterium T–DNA Genes in Tobacco and Maize, The Plant Cell, May 1996, pp. 873–886, vol. 8, American Society of Plant Physiologists.

O'Gorman et al. Recombinase–Mediated Gene Activation and Site–Specific Integration in Mammalian Cells, *Science,* Mar. 15, 1991, pp. 1351–1355, vol. 251, Salk Institute for Biological Studies, La Jolla, California.

O'Gorman et al., Protamine–Cre Recombinase Transgenes Efficiently Recombine Target Sequences in the Male Germ Line of Mice, but not in Embryonic Stem Cells, *Proc. Natl. Acad. Sci. USA* (Dec. 1997) pp. 14602–14607 vol. 94 Gene Expression Lab., The Salk Inst. For Biological Studies, San Diego, CA.

Ow et al., Genome Manipulation Through Site–Specific Recombination, Critical Reviews in Plant Sciences, (1995), pp 239–261, vol. 14(3).

Raineri et al., "VirA, The Plant–Signal Receptor, is Responsible for the T1 Plasmid–specific Transfer of DNA to Maize by Agrobacterium" *Microbiology* (1993) pp. 3549–3553, vol. 90.

Russsell, et al., Directed Esicsion of a Transgene from the Plant Genome, Mol. Genet Genet (1992), pp. 49–59, vol. 234 Central Res. and Devel. And Agric. Prod. Du Pont Experimental Station, Wilmington, DE.

Sadowski et al., "Site Specific Genetic Recombination: Hops, Flips, and Flops," *FASEB,* 1993, pp. 760–767, vol. 7.

Sauer (1992) "Identification of Cryptic lox Sites in the Yeast Genome by Selection for Cre–mediated Chromosome Translocations that Confer Multiple Drug Resistance", *J. Mol. Biol. 223:*911–928.

Sauer, B., "Site–Specific Recombination: Developments and Applications," *Current Opinion in Biotechnology,* 1994, pp. 521–527, vol. 5.

Schlake et al,. "Use of Mutated FLP Recognition Target (FRT) Sites for the Exchange of Expression Cassettes at Defined Chromosomal Loci," *Biochemistry* (1994) pp. 12746–12751 vol. 33:GBF, Braunschweig–Stockheim, Germany.

Scholthof et al. (1996) "Plant Virus Gene Vectors For Transient Expression of Foreign Proteins in Plants", *Annu. Rev. of Phytopathohl 34*:299–323.

Seibler et al. (1997) "Double–Reciprocal Crossover Mediated by FLP–Recombinase: A Concept and an Assay", *Biochemistry 36*;1740–1747.

Senecoff et al. Directionality in FLP Protein–Promoted Site–Specific Recombination Is Mediated by DNA–DNA Pairing, *J. Biol. Chem.*, Jun. 5, 1986, pp. 7380–7386, vol. 261(16), The American Society of Biological Chemists, Inc., Madison, Wisconsin.

Senecoff et al. (1988) "DNA Recognition By The FLP Recombinase of the Yeast 2 μ Plasmid", *J. Mol. Biol. 201*:406–421.

Snaith et al., Multiple Cloning Sites Carrying loxP and FRT Recognition Sites for the Cre and Flp Site–Specific Recombinases, Gene, 1995, pp. 173–174, vol. 166.

Storici et al. (1997) "Molecular Engineering with the FRT Sequence of the Yeast 2 μm Plasmid: [cir] Segregant Enrichment by Counterselection for 2 μm Site–Specific Recombination", *Gene 195*:245–255.

Timmermans et al. (1992) "Trans Replication and High Copy Numbers of Wheat Dwarf Virus Vectors in Maize Cells", *Nucleic Acids Research 20(15)*:4047–4054.

Ugaki et al. (1991) "Replication of a Germinivirus Derived Shuttle Vector in Maize Endosperm Cells", *Nucleic Acids Research 19(2)*:371–377.

Umlauf et al,. "The Functional Significance of DNA Sequence Structure in a Site–Specific Genetic Recombination Reaction," 1988, pp. 1845–1852, IRL Press Limited, Oxford, England.

Zhang et al., Inducible Site–Directed Recombination in Mouse Embryonic Stem Cells, *Nucleic Acids Research (1996)* pp. 543–548 vol. 24(4) Oxford University Press.

U.S. Appl. No. 09/455,051, filed Dec. 6, 1999, Baszczynski et al., Whole Document.

U.S. Appl. No. 10/430,907, filed May 7, 2003, Baszczynski et al., Whole Document.

U.S. Appl. No. 10/430,908, filed May 7, 2003, Baszczynski et al., Whole Document.

U.S. Appl. No. 10/440,030, filed May 16, 2003, Baszczynski et al., Whole Document.

U.S. Appl. No. 10/639,751, filed Aug. 12, 2003, Baszczynski et al., Whole Document.

Campbell, W.H., and G. Gowri, "Codon Usage in Higher Plants, Green Algae, and Cyanobacteria," *Plant Physiol.,* 1990, pp. 1–11, vol. 92.

Chiu, W., et al., "Engineered GFP as a Vital Reporter in Plants," *Current Biol.,* 1996, pp. 325–330, vol. 6(3).

Dildine, S.L., et al., "A Chimeric Ty3/Moloney Murine Leukemia Virus Integrase Protein is Active *In Vivo,*" *J. of Virology,* 1998, pp. 4297–4307, vol. 72(5).

Esposito, M.S., et al., "Recombinators, Recominases and Recombination Genes of Yeasts," *Curr. Genetics,* 1994, pp. 1–11, vol. 25.

Fry, et al., "Transformation of *Brassica napus* with *Abrobacterium tumefaciens* Based Vectors," *Plant Cell Rep.,* 1987, pp. 321–325, vol. 6.

Grimsley, et al., "Agroinfection," an Alternative Route for Visual Invection of Plants by Using the Ti Plasmid, *Proc. Natl. Acad. Sci.,* USA, 1986, pp. 3282–3286, vol. 83.

Hayes, et al., "Agroinfection of Nictiana spp. With Cloned DNA of Tomato Golden Mosaic Virus," *J. Gen. Virol.,* 1988, pp. 1487–1496, vol. 69, SGM.

Lloyd, A.M., and R.W. Davis, "Functional Expression of the Yeast FLP/FRT Site–Specific Recombination System in *Nicotiana tabacum*," *Mol. Gen. Genet.,* 1994, pp. 653–657, vol. 242.

Murray, et al., "Condon Usage in Plant Genes," *Nucleic Acid Research,* 1989, pp. 477–490, vol. 17(2).

Osborne, B.I., et al., "A System for Insertional Mutagenesis and Chromosomal Rearrangement Using the Ds Transposon and Cre–lox," *The Plant Journal,* 1995, pp. 687–701, vol. 7(4).

Shen and Hohn, "Excision of a Transposable Element from a Viral Vector Introduced into Maize Plants by Agroinfection," *The Plant Journal,* 1992, pp. 35–42, vol. 2(1), Friedrich Miescher–Institute, Basel.

Timmermans, et al., "Geminiviruses and Their Uses as Extrachromosomal Replicons," *Annu. Rev. Plant Physiol. Plant Mol. Biol.,* 1994, pp. 79–112, vol. 45.

Ugaki, M., et al., "Replication of a Geminivirus Derived Shuttle Vector in Maize Endosperm Cells," *Nucleic Acids Research,* 1990, pp. 371–377, vol. 19(2).

Fisch, I., "A Strategy of Exon Shuffling for Making Large Peptide Repertoires Displayed on Filamentous Bacteriophage," *Proc. Natl. Acad. Sci.,* 1996, vol. 93, pp. 7761–7766.

\* cited by examiner

SEQUENCE LISTING

```
<160> NUMBER OF SEQ ID NOS: 6

<210> SEQ ID NO 1
<211> LENGTH: 34
<212> TYPE: DNA
<213> ORGANISM: Artificial Sequence
<220> FEATURE:
<223> OTHER INFORMATION: wild type loxP recombination site

<400> SEQUENCE: 1
ataacttcgt atagcataca ttatacgaag ttat                              34

<210> SEQ ID NO 2
<211> LENGTH: 47
<212> TYPE: DNA
<213> ORGANISM: Artificial Sequence
<220> FEATURE:
<223> OTHER INFORMATION: wild type FRT recombination site

<400> SEQUENCE: 2
gaagttccta tactttctag agaataggaa cttggaatag gaacttc                47

<210> SEQ ID NO 3
<211> LENGTH: 34
<212> TYPE: DNA
<213> ORGANISM: Artificial Sequence
<220> FEATURE:
<223> OTHER INFORMATION: minimal FRT recombination site

<400> SEQUENCE: 3
gaagttccta ttctctagaa agtataggaa cttc                              34

<210> SEQ ID NO 4
<211> LENGTH: 69
<212> TYPE: DNA
<213> ORGANISM: Artificial Sequence
<220> FEATURE:
<223> OTHER INFORMATION: FRT 5

<400> SEQUENCE: 4
ccatggctag cgaagttcct attccgaagt tcctattctt caaaaggtat aggaacttca   60
gtactcgag                                                          69

<210> SEQ ID NO 5
<211> LENGTH: 72
<212> TYPE: DNA
```

```
<213> ORGANISM: Artificial Sequence
<220> FEATURE:
<223> OTHER INFORMATION: FRT 6

<400> SEQUENCE: 5
ccatggctag cgaagttcct attccgaagt tcctattctt caaaaagtat aggaacttca        60
gacgtcctcg ag                                                           72

<210> SEQ ID NO 6
<211> LENGTH: 72
<212> TYPE: DNA
<213> ORGANISM: Artificial Sequence
<220> FEATURE:
<223> OTHER INFORMATION: FRT 7

<400> SEQUENCE: 6
ccatggctag cgaagttcct attccgaagt tcctattctt caataagtat aggaacttca       60
ctagttctcg ag                                                           72
```

MOBILIZATION OF VIRAL GENOMES FROM T-DNA USING SITE-SPECIFIC RECOMBINATION SYSTEMS

CROSS-REFERENCE TO RELATED APPLICATION

This application is a continuation application of U.S. patent application Ser. No. 09/411,826, filed Oct. 1, 1999, now U.S. Pat. No. 6,664,108 which is a Divisional of Ser. No. 09/193,475 filed Nov. 17, 1998 now U.S. Pat. No. 6,300,545, which claims the benefit of U.S. Provisional Application Ser. No. 60/099,461, filed Sep. 8, 1998, U.S. Provisional Application Ser. No. 60/065,627, filed Nov. 18, 1997, U.S. Provisional Application Ser. No. 60/065,613, filed Nov. 18, 1997, all of which are herein incorporated by reference.

FIELD OF THE INVENTION

The present invention relates to plant molecular biology. More specifically, the invention relates to methods and compositions for increasing the efficiency of excision of viral replicon from T-DNA that is transferred to a plant by agroinfection.

BACKGROUND OF THE INVENTION

*Agrobacterium* harboring a Ti or a Ri plasmid can efficiently transfer a portion of these plasmids, the T-DNA, into plant cells at the site of a wound. Transfer of the T-DNA into the plant cell is induced by signal compounds present at the site of a plant wound and requires T-DNA border sequences at both ends of the T-DNA and trans-acting virulence gene products (vir) encoded by the Ti or Ri plasmid. The transferred T-DNA is then targeted to the nucleus and integrated into the plant genome. A tumor, crown gall, forms at the site of inoculation in most dicotyledonous plants.

Tumor formation results from the expression of T-DNA oncogenes encoding the growth factors auxin and cytokinin which promote plant cell proliferation. In order for these oncogenes to be expressed, the T-DNA must first integrate into the genome of the plant. Tumor formation is limited to dicotyledonous plants because the T-DNA, while transferred into the cells of monocots, is either not normally integrated into the genome of monocotyledonous plants or is integrated and silenced.

By inserting a viral genome into the T-DNA, *Agrobacterium* can be used to mediate the viral infection of plants. Following transfer of the T-DNA to the plant cell, excision of the viral genome from the T-DNA (mobilization) is required for successful viral infection. This *Agrobacterium*-mediated method for introducing a virus into a plant host is known as agroinfection (for a review, see Grimsley, "Agroinfection" pp. 325–342, in *Methods in Molecular Biology, vol 44: Agrobacterium Protocols,* ed. Gartland and Davey, Humana Press, Inc., Totowa, N.J.; and Grimsley (1990) *Physiol. Plant.* 79:147–153, the contents of which are incorporated herein by reference). Upon entry into the plant cell nucleus, a unit length circular viral genome that is capable of initiating systemic infection is mobilized from the T-DNA. Integration of the T-DNA into the plant genome is not required for this event. Two non-exclusive mechanisms, intramolecular homologous recombination and replicative release, have been proposed for this release of circular viral genomes or replication intermediates from T-DNA. The replicative release of viral genomes by the rolling-circle replication mechanism has been demonstrated for the mobilization of geminivirus genomes from T-DNA (Stenger et al. (1991) *Proc. Natl. Acad. Sci.* 88:8029–8033). Release of geminivirus via homologous recombination between tandemly repeated genomes has also been demonstrated (Lazarowitz et al. (1989) *EMBO J.* 8:1023–1032).

Release by either of the above mechanisms requires the presence of tandem directly repeated copies of the viral replicon in the T-DNA. A circular viral replicon may be excised from the T-DNA by intramolecular homologous recombination between the repeated genomes. For replicative release, two origin of replication sequences must be present to initiate and complete the replication process. Both mechanisms of mobilization are complex biochemical processes that may be attenuated by a number of factors which in turn affect the efficiency of viral excision. Furthermore, tandem dimers of viral DNA are often difficult to construct and are unstable in recombination proficient host cells.

Agroinfection has been reported in a number of publications as a successful method for inducing systemic viral infections in plant cells, including monocotyledonous plants such as maize (Heath et al. (1997) *Mol. Plant-Microbe Interact.* 10:221–227, Grimsley et al. (1989) *Mol. Gen. Genet.* 217:309–316, the contents of which are incorporated herein by reference). In many instances, particularly when naked viral nucleic acid is non-infectious, agroinfection is the only way of transforming a plant with cloned viral DNA. Even where naked viral nucleic acid is infectious, agroinfection is frequently used because it is relatively efficient and does not require the production of large amounts of plasmid or viral DNA. Agroinfection has been used to study viral replication and recombination, in the investigation of viral gene functions, for the production of autonomously replicating viral vectors, for transient expression of genes inserted into T-DNA, for integration of DNA into a plant genome, for production of virus resistant plants, for the study of transposable elements and for the determination of tissue-specific susceptibility to T-DNA transfer.

The development of plant virus gene vectors for expression of foreign genes in plants provides a means to provide high levels of gene expression within a short time. The benefits of virus-based transient RNA and DNA replicons include rapid and convenient engineering coupled with flexibility for expeditious application in various plant species. In this manner, autonomously replicating viruses offer numerous advantages for use as vehicles for transient expression of foreign genes, including their characteristic high levels of multiplication and concomitant levels of transient gene expression. Accordingly, it would be beneficial to provide methods that facilitate the construction of vectors for agroinfection, provide flexibility in designing viral vectors for genetic transformation of plant cells and increase the efficiency of mobilization of viral replicons from T-DNA and the copy number of a DNA sequence of interest associated with the viral replicon.

The present invention accomplishes these objectives by providing methods and compositions for the mobilization of viral replicon from T-DNA via site-specific recombination systems. Site-specific recombination-mediated excision of DNA fragments from chromosomal or extrachromosomal DNA molecules has been described for a number of site-specific recombination systems and plant species. See Russell et al. (1992) *Mol. Gen. Genet.* 234:49–59; Lyznik et al. (1996) *Nucleic Acids Res.* 24:3784–3789; and Dale et al. (1991) *Proc. Natl. Acad. Sci.* 88:10558–10562 the contents of which are incorporated by reference. However, mobilization of viral vectors from T-DNA via site-specific recombination has not previously been applied to agro-mediated transformation.

SUMMARY OF THE INVENTION

The invention relates to methods and compositions for site-specific recombinase-mediated mobilization of viral replicons and associated DNAs of interest from T-DNA. The methods of the invention comprise *Agrobacterium*-mediated transfer of T-DNA to a plant cell, wherein the T-DNA contains a viral replicon flanked by directly repeated target sites for a site-specific recombinase and optionally a DNA of interest linked to the viral replicon. The DNA of interest may also contain a non-identical target site for the recombinase. An expression cassette for the site-specific recombinase is present on the T-DNA or the plant genome, or is transiently introduced into the plant cell. Expression of the site-specific recombinase in the plant cell results in excision of the viral replicon and the associated DNA of interest. The viral replicon and DNA of interest are then replicated to high copy number in the host plant cell.

The compositions of the invention comprise nucleic acids, such as T-DNAs containing a viral DNA flanked by directly repeated target sites for a site-specific recombinase. The nucleic acids of the invention may additionally contain expression cassettes encoding the cognate site-specific recombinase for the target sites flanking the viral genome. The compositions of the invention further comprise *Agrobacterium* containing the nucleic acids of the invention.

The compositions and methods of the invention have use in providing high copy numbers of a DNA of interest for transient expression or for integration into a plant chromosome, in simplifying the construction and stable maintenance of vectors for agro-mediated transformation of plants and in increasing the efficiency of agroinfection.

DETAILED DESCRIPTION OF THE INVENTION

Figure 1:
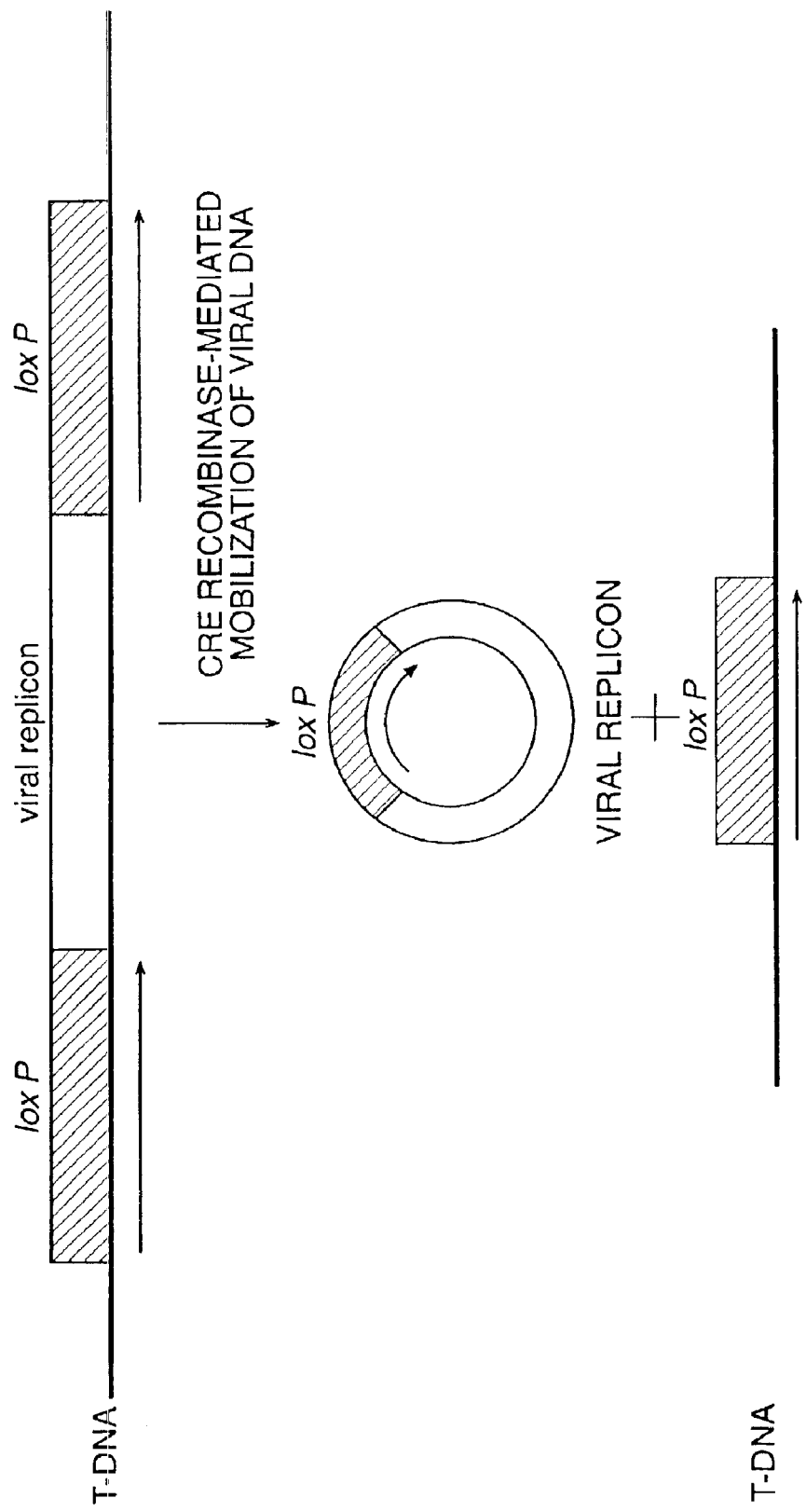
FIG. 1 schematically illustrates a model of mobilization of a viral replicon from T-DNA by loxP/Cre site-specific recombination.

The invention is directed to methods and compositions for the mobilization of viral DNA from T-DNA. In the methods of the invention, a viral replicon flanked by directly repeated target sites for a site-specific recombinase is inserted into a T-DNA carried by an *Agrobacterium* replicon. The T-DNA is transferred into the cell of a plant by agro-mediated transfer. Expression of the site-specific recombinase in the infected plant cell will result in excision of a circular viral replicon from the transferred T-DNA (FIG. 1). Replication of this viral replicon will result in a high number of copies of the replicon. Systemic infection of the plant may take place if the replicon encodes infectious viral particles. Accordingly, the methods of the invention have use in the production of viral DNA and/or in promoting systemic viral infection of a plant.

Thus, the invention is directed to a method for mobilizing a viral replicon from a T-DNA, comprising:

a) providing an *Agrobacterium* replicon having a T-DNA, wherein said T-DNA contains a viral replicon flanked by directly repeated target sites for a site-specific recombinase; and b) infecting a cell of a plant with an *Agrobacterium* carrying said *Agrobacterium* replicon under conditions that allow transfer of said T-DNA and expression of said recombinase in said cell;

wherein said cell, said T-DNA, or said viral replicon contains a nucleotide sequence encoding said recombinase or an active fragment or variant thereof, and said nucleotide sequence is operably linked to a promoter that drives expression in said cell.

If a DNA of interest has been inserted into the viral replicon, or between the viral replicon and a target site for a site-specific recombinase, the DNA of interest will also be replicated to high copy. The high copy number of the DNA of interest increases the efficiency of integration of this DNA into the genome, or the level of transient expression of a gene encoded by the DNA of interest. Thus, in another aspect, the invention provides a method for providing to a plant cell a plurality of copies of a DNA sequence of interest, comprising:

a) providing an *Agrobacterium* replicon having a T-DNA, wherein said T-DNA contains in a 5' to 3' or 3' to 5' orientation, a first target site for a site-specific recombinase, a viral replicon, said DNA sequence of interest, and a second target site for said recombinase in direct repeat with said first target site, wherein said first and second target sites are identical; and b) infecting a cell of a plant with an *Agrobacterium* carrying said *Agrobacterium* replicon under conditions that allow transfer of said T-DNA and expression of said recombinase in said cell; wherein said cell, said T-DNA, or said viral replicon contains a nucleotide sequence encoding said recombinase or an active fragment or variant thereof, and said nucleotide sequence is operably linked to a promoter that drives expression in said cell.

The methods of the invention are useful for providing a high copy number of a DNA of interest for site-specific integration into a plant chromosome. In this case, the plant chromosome will contain one or more target sites for a site-specific recombinase. Depending on the substrates, the recombination event could consist of a single or a double cross-over event. In the simplest case, the plant chromosome and the excised viral replicon each contain a single target site. Site-specific recombination between these two target sites results in the insertion of the viral replicon and any associated DNA of interest into the plant chromosome.

Figure 2:
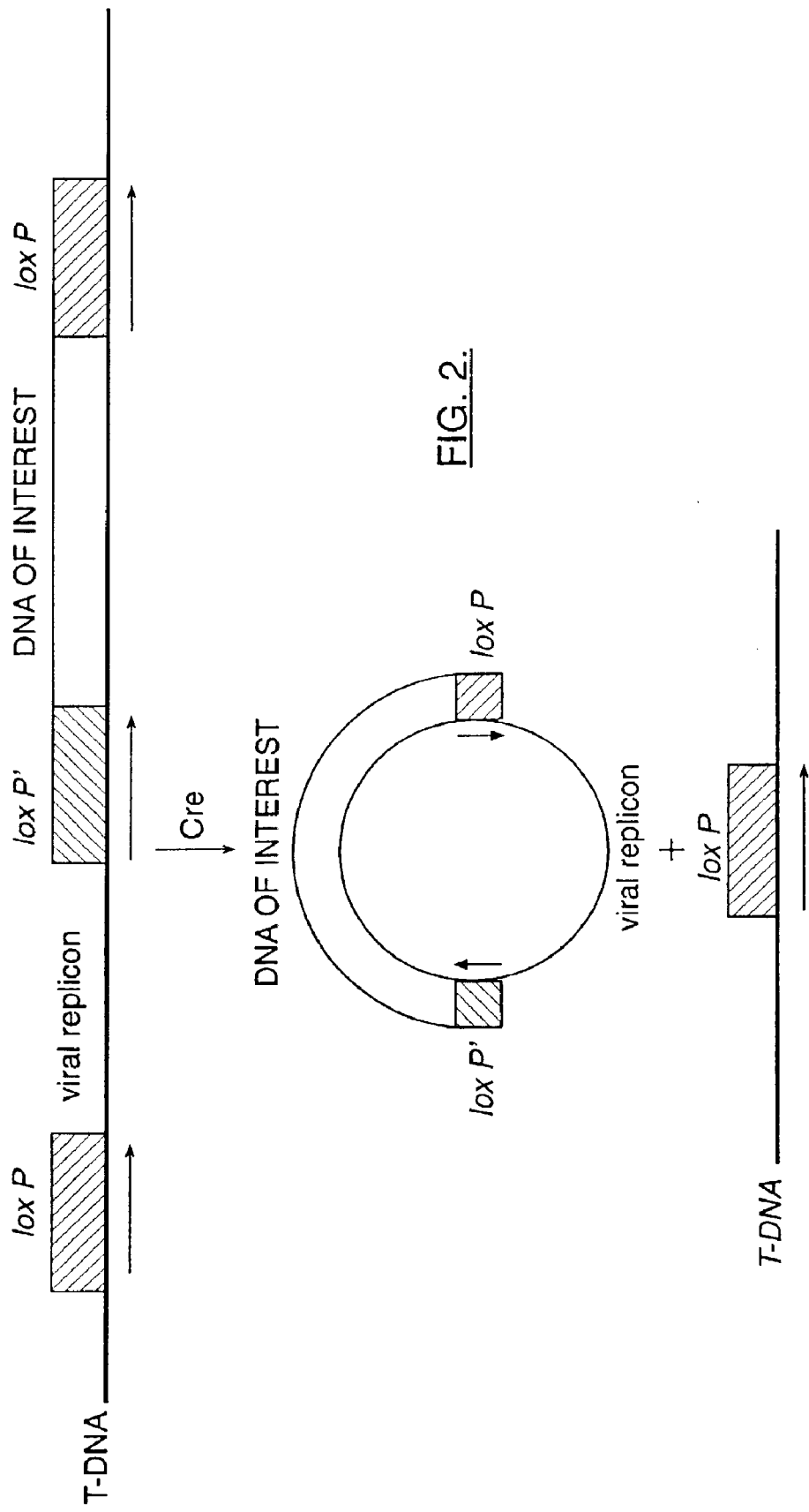
FIG. 2 schematically illustrates Cre-mediated site-specific excision of a viral DNA and DNA of interest from a T-DNA.
Figure 3:
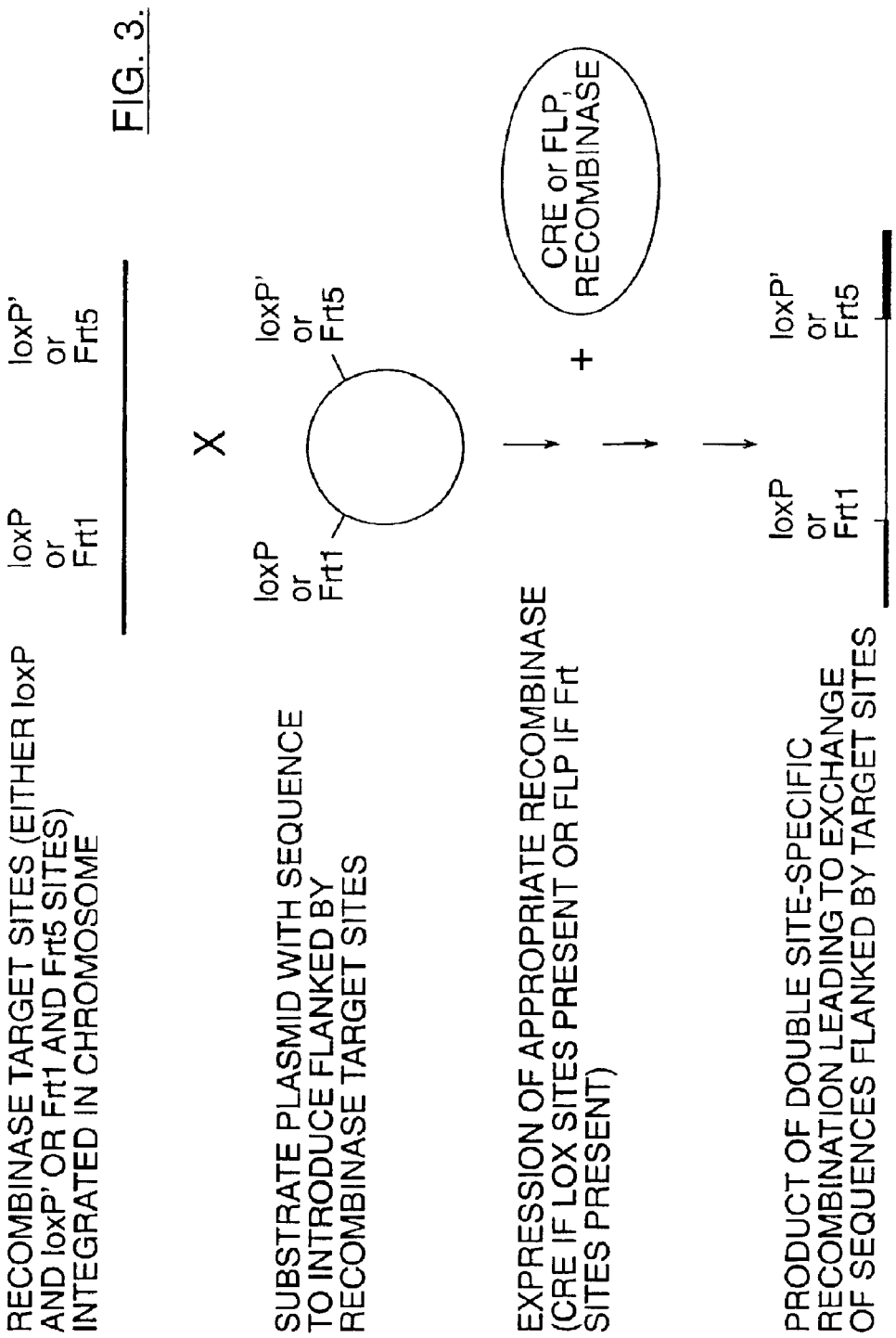
FIG. 3 schematically illustrates the integration of DNA into a chromosome by double site-specific recombination.

The inclusion of a non-identical target site between the viral replicon and the DNA of interest allows integration of the DNA of interest into a plant genome having a corresponding target site, without concomitant insertion of the viral replicon. In this method, the distal ends of the viral replicon and the DNA of interest are flanked by identical target sites. Recombination between the identical target sites results in excision of a circular viral replicon containing the DNA of interest flanked by non-identical target sites for the recombinase (FIG. 2). For targeted insertion of the DNA of interest, the same two non-identical target sites are present in the target organisms genome, thereby establishing a target site for insertion of the DNA of interest. A double crossover event resulting from site-specific recombination between the identical target sites on the host genome and the DNA of interest results in the insertion of the DNA of interest into the chromosome of the target organism, free of the viral replicon (FIG. 3). Such methods are discussed in detail in the provisional application, Ser. No 60/065,613, filed Nov. 18, 1997, the contents of which are incorporated herein by reference.

Thus, in a further aspect, the invention provides a method for providing to a plant cell a plurality of copies of a DNA sequence of interest flanked by nonidentical target sites for a site-specific recombinase, comprising:

a) providing an *Agrobacterium* replicon having a T-DNA, wherein said T-DNA contains in a 5' to 3' or 3' to 5' orientation, a first target site for said recombinase, a viral replicon, a second target site for said recombinase, said DNA sequence of interest, and a third target site for said recombinase, wherein said first and third target sites are directly repeated and identical with respect to each other, and said second target site is nonidentical to said first and third target sites; and b) infecting a cell of a plant with an *Agrobacterium* carrying said *Agrobacterium* replicon under conditions that allow transfer of said T-DNA and expression of said recombinase in said cell;

wherein said cell, said T-DNA, or said viral replicon contains a nucleotide sequence encoding said or an active fragment or variant thereof, and said nucleotide sequence is operably linked to a promoter that drives expression in said cell.

The compositions of the invention comprise T-DNAs containing a viral replicon flanked by directly repeated target sites for a site-specific recombinase. In another aspect, the compositions of the invention comprise a T-DNA containing in a 5' to 3' or 3' to 5' orientation, a first target site for said recombinase, a viral replicon, a second target site for said recombinase, said DNA sequence of interest, and a third target site for said recombinase, wherein said first and third target sites are directly repeated and identical with respect to each other, and said second target site is nonidentical to said first and third target sites. The T-DNAs of the invention may further comprise nucleotide sequence encoding a site-specific recombinase, wherein the nucleotide sequence is operably linked to a promoter that drives expression in a plant cell. The compositions of the invention further comprise replicons containing these T-DNAs and *Agrobacterium* containing these replicons.

By "mobilization of a viral replicon" is meant excision of a viral replicon from a T-DNA sequence after it has been transferred to a plant cell. In the methods of the invention, mobilization of viral DNA is accomplished by conservative site-specific recombination between directly repeated target sites flanking the viral DNA. In one embodiment, the resulting product is a circularized viral DNA containing one copy of the target site (see FIG. 1).

By "viral replicon" is meant double-stranded DNA from a virus having a double stranded DNA genome or replication intermediate. The excised viral DNA is capable of acting as a replicon or replication intermediate, either independently, or with factors supplied in trans. The viral DNA may or may not encode infectious viral particles and furthermore may contain insertions, deletions, substitutions, rearrangements or other modifications. The viral DNA may contain heterologous DNA. In this case, heterologous DNA refers to any non-viral DNA or DNA from a different virus. For example, the heterologous DNA may comprise an expression cassette for a protein or RNA of interest.

Viral replicons suitable for use in the methods and compositions of the invention include those of viruses having a circular DNA genome or replication intermediate, such as: Abuitilon mosaic virus (AbMV), African cassava mosaic virus (ACMV), banana streak virus (BSV), bean dwarf mosaic (BDMV), bean golden mosaic virus (BGMV), beet curly top virus (BCTV), beet western yellows virus (BWYV) and other luteoviruses, cassava latent virus (CLV), carnation etched virus (CERV), cauliflower mosaic virus (CaMV), chloris striate mosaic (CSMV), commelina yellow mottle virus (CoYMV), cucumber mosaic virus (CMV), dahlia mosaic virus (DaMV), digitaria streak virus (DSV), figwort mosaic virus (FMV), hop stunt viroid (HSV), maize streak virus (MSV), mirabilias mosaic virus (MMV), miscanthus streak virus (MiSV), potato stunt tuber virus (PSTV), panicum streak virus (PSV), potato yellow mosaic virus (PYMV), rice tungro bacilliform virus (RTBV), soybean chlorotic mottle virus (SoyCMV), squash leaf curl virus (SqLCV), strawberry vein banding virus (SVBV), sugarcane streak virus (SSV), thistle mottle virus (ThMV), tobacco mosaic virus (TMV), tomato golden mosaic virus (TMGV), tomato mottle virus (TMoV), tobacco ringspot virus (TobRV), tobacco yellow dwarf virus (TobYDV), tomato leaf curl virus (TLCV), tomato yellow leaf curl virus (TYLCV), tomato yellow leaf curl virus-Thialand (TYLCV-t) and wheat dwarf virus (WDV) and derivatives thereof. Preferably the viral replicon is from MSV, WDV, TGMV or TMV.

By "T-DNA" is meant the T-DNA of an *Agrobacterium tumefaciens* Ti plasmid or from an *Agrobacterium rhizogenes* Ri plasmid, or a derivative thereof The T-DNA may comprise an entire T-DNA, but need only comprise the minimal sequences required in cis for transfer (i.e., the right and the left T-DNA border sequences). The T-DNAs of the invention have inserted into them, anywhere between the right and left border sequences, a viral DNA flanked by target sites for a site-specific recombinase. The T-DNA may contain deletions, substitutions and/or additional insertions of DNA other than the viral genome and target sites. Preferably the T-DNA contains an expression cassette for the cognate recombinase of the target sites flanking the viral DNA. The sequences encoding factors required in trans for transfer of the T-DNA into a plant cell, such as vir genes, may be inserted into the T-DNA, or may be present on the same replicon as the T-DNA, or in trans on a compatible replicon in the *Agrobacterium* host. Preferably the trans acting factors required for T-DNA transfer are present on the same replicon as the T-DNA.

By "*Agrobacterium* replicon" is meant any replicon (e.g., plasmid or other vector) that is capable of being stably maintained in an *Agrobacterium* host. Such replicons include the *Agrobacterium* chromosome, *Agrobacterium* plasmids, cosmids, phagemids, etc., derivatives thereof, and any other vector capable of stable replication in *Agrobacterium*. For example, a binary vector suitable for both *Agrobacterium*-mediated transfer and for facile recombinant manipulations and replication in other organisms is useful in the methods and compositions of the invention. Preferably the replicon is a Ti or Ri plasmid or a derivative thereof.

Figure 4:
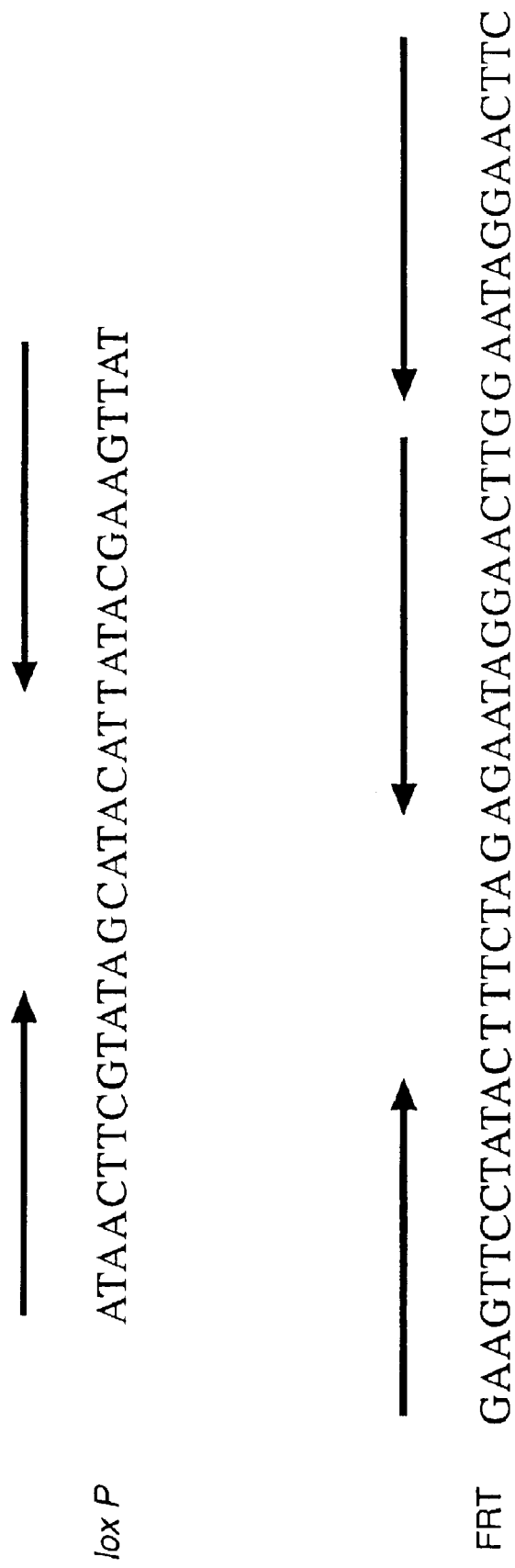
FIG. 4 shows the 5' to 3' sequences of the loxP (SEQ ID NO:1) and FRT (SEQ ID NO:2) sites.

In the compositions and methods of the invention, the viral replicon is flanked by directly repeated target sites for a site-specific recombinase. By "flanked by" is meant that the target sites may be directly contiguous with the viral DNA or there may be one or more intervening sequences present between one or both ends of the viral DNA and the target sites. Intervening sequences of particular interest would include linkers, adapters, selectable markers and/or other sites which aid in vector construction or analysis and expression cassette for a gene of interest. Target sites for site-specific recombinases are known to those skilled in the art and are discussed in provisional application 60/065,613, filed on Nov. 18, 1997. Examples of target sites include, but are not limited to FRT, FRT1, FRT5, FRT6, FRT7, other FRT mutants, loxP, loxP mutants, and the like. The loxP and FRT sites are shown in FIG. 4.

By "directly repeated" is meant that the target sites that flank the viral DNA are arranged in the same orientation, so that recombination between these sites results in excision, rather than inversion, of the viral DNA.

By "site-specific recombinase" is meant any enzyme capable of being functionally expressed in plants, that catalyzes conservative site-specific recombination between its corresponding target sites. For reviews of site-specific recombinases, see Sauer (1994) *Current Opinion in Biotechnology* 5:521–527; Sadowski (1993) *FASEB* 7:760–767; the contents of which are incorporated herein by reference. Methods of using site-specific recombination systems to excise DNA fragments from chromosomal or extrachromosomal plant DNA are known to those skilled in the art. The bacteriophage P1 loxP-Cre and the *Saccharomyces* 2μ plasmid FRT/FLP site-specific recombinations systems have been extensively studied. For example, Russell et al. (1992, *Mol. Gen. Genet.* 234:49–59) describe the excision of selectable markers from tobacco and *Arabidopsis* genomes using the loxP-Cre site-specific recombination system.

It is furthermore recognized that the recombinase, which is used in the invention, will depend upon the target sites of the transformed organism and the targeting cassette. That is, if FRT sites are utilized, the FLP recombinase will be needed. In the same manner, where lox sites are utilized, the Cre recombinase is required. If the non-identical target sites comprise both a FRT and a lox site, both the FLP and Cre recombinase or a chimeric recombinase having both Cre and FLP functions, as described in the concurrently filed provisional application entitled "A NOVEL MTHOD FOR THE INTEGRATION OF FOREIGN DNA INTO EUKARYOTIC GENOMES," will be required in the plant cell.

The site-specific recombinase may be a naturally occurring recombinase or an active fragment derivative thereof. Site-specific recombinases useful in the methods and compositions of the invention, include recombinases from the integrase and resolvase families, derivatives thereof, and any other naturally occurring or recombinantly produced enzyme or derivative thereof, that catalyzes conservative site-specific recombination between specified DNA sites. The integrase family of recombinases has over thirty members and includes FLP, Cre, Int and R. The resolvase family includes γδ resolvase. Recombinant enzymes that catalyze site-specific conservative recombination include moFLP, described in co-pending application Ser. No. 08/972,258, now U.S. Pat. No. 5,929,301. Other recombinases include moCre described in U.S. patent application Ser. No. 09/193,503, filed Nov. 17, 1998, the contents of which are incorporated herein by reference. Preferably, the recombinase is one that does not require cofactors or a supercoiled substrate. Such recombinases include Cre, FLP moflp, and moCre.

moflp is derived from the *Saccharomyces* 2μ plasmid FLP recombinase, but is encoded by a nucleic acid sequence utilizing maize-preferred codons. While the moflp nucleic acid sequence includes preferred codons for expression of amino acids in maize, it is understood that a useful sequence may contain codons occurring in maize with less than the highest reported maize codon frequencies.

The site-specific recombinases and sequences encoding them that are used in the methods and compositions of the invention may be variants of naturally occurring recombinases and the genes encoding them. The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. One of ordinary skill will recognize that each codon in a nucleic acid (except AUG, which is ordinarily the only codon for methionine) can be modified to yield a functionally identical molecule.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See Creighton (1984) Proteins, W. H. Freeman and Company.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucl. Acids Res.* 17:477–498; and Campbell et al. (1990) *Plant Physiol.* 92:1). Thus, the maize preferred codon for a particular amino acid may be derived from known gene sequences from maize. Maize codon usage for 28 genes from maize plants are listed in Table 4 of Murray et al., supra.

The FLP recombinase gene from yeast (*Saccharomyces cerevisiae*) is commercially available in plasmid pOG44 from Stratagene Cloning Systems (11011 North Torrey Pines Road, La Jolla, Calif. 92037). Similarly, the sequences of many other site specific recombinases and their cognate target sites are publicly or commercially available.

Genes encoding site-specific recombinases, viral DNA, T-DNA and target sites can be made using (a) standard recombinant methods, (b) synthetic techniques, or combinations thereof. Use of cloning vectors, expression vectors, adapters, and linkers is well known in the art and can be found in such references as Sambrook et al., *Molecular Cloning: A Laboratory Manual,* 2nd ed. (Cold Spring Harbor, N.Y., 1989). A variety of strategies are available for ligating fragments of DNA, the choice of which depends on the nature of the termini of the DNA fragments and which choices can be readily made by those of skill in the art. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.). Genes encoding FLP can be obtained, for example, by synthesizing the genes with mutually priming long oligonucleotides. See, for example, Ausubel et al. (eds.), *Current Protocols In Molecular Biology,* pages 8.2.8 to 8.2.13, Wiley Interscience (1990). Also, see Wosniak et al. (1987) *Gene* 60:115. Moreover, current techniques using the polymerase chain reaction provide the ability to synthesize genes as large as 1.8 kilobases in length (Adang et al. (1993) *Plant Mol. Biol.* 21:1131; Bombat et al. (1993) *PCR Methods and Applications* 2:266).

Rather than use full length recombinases, functional fragments of site-specific recombinases may be used in the methods and compositions of the invention. Functional fragments of site-specific recombinases can be identified using a variety of techniques such as restriction analysis, Southern analysis, primer extension analysis, and DNA sequence analysis. Primer extension analysis or S1 nuclease protection analysis, for example, can be used to localize the putative start site of transcription of the cloned gene. Ausubel at pages 4.8.1 to 4.8.5; Walmsley et al, Quantitative and Qualitative Analysis of Exogenous Gene Expression by the S1 Nuclease Protection Assay, in Methods In Molecular Biology, Vol. 7: Gene Transfer and Expression Protocols, Murray (ed.), pages 271–281 (Humana Press, Inc. 1991). For examples, functional fragments of the FLP protein may be identified by their ability, upon introduction to cells containing appropriate FRT substrates, to catalyze site-specific recombination (for example, excision of an FRT-flanked sequence which upon removal will activate an assayable marker gene.

The general approach of such functional analysis involves subcloning DNA fragments of a genomic clone, cDNA clone or synthesized gene sequence into an expression vector, introducing the expression vector into a heterologous host, and screening to detect the product of recombination (i.e. using restriction analysis to verify the product of recombination at the nucleic acid level, or relying on an assay system for recombination as described above). Methods for generating fragments of a CDNA or genomic clone are well known. Variants of an isolated DNA encoding a site-specific recombinase can be produced by deleting, adding and/or substituting nucleotides. Such variants can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), *Directed Mutagenesis: A Practical approach,* (IRL Press, 1991).

The nucleic acid sequence encoding the site-specific recombinase is operably linked to a promoter that drives expression in a plant. As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria genes that are expressed in plant cells such as those of *Agrobacterium* or *Rhizobium.* Both heterologous and non-heterologous (i.e., endogenous) promoters can be employed to direct expression of a sequence encoding a site-specific recombinase. The promoter may be constitutive, inducible or tissue specific.

Many different constitutive promoters can be utilized in the instant invention. Exemplary constitutive promoters include the promoters from plant viruses such as the 35S promoter from CaMV (Odell et al. (1985) *Nature* 313:810–812) and the promoters from such gene as rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); maize H3 histone (Lepetit et al. (1992) *Mol. Gen. Genet.* 231:276–285 and Atanassova et al. (1992) *Plant Journal* 2(3):291–300); the 1'- or 2'-promoter derived from T-DNA of *Agrobacterium tumefaciens,* the ubiquitin 1 promoter, the Smas promoter, the cinnamyl alcohol dehydrogenase promoter (U.S. Pat. No. 5,683,439), the Nos promoter, the Pemu promoter, the rubisco promoter, the GRP1-8 promoter, and other transcription initiation regions from various plant genes known to those of skill. The ALS promoter, a XbaI/NcoI fragment 5-prime to the *Brassica napus* ALS3 structural gene (or a nucleotide sequence that has substantial sequence similarity to said XbaI/NcoI fragment), represents a particularly useful constitutive promoter for dicots. (See co-pending Pioneer Hi-Bred International U.S. patent application Ser. No. 08/409,297, now U.S. Pat. No. 5,659,026).

A variety of inducible promoters can be used in the instant invention. See Ward et al. (1993) *Plant Mol. Biol.* 22:361–366. Exemplary inducible promoters include that from the ACE1 system which responds to copper (Mett et al. (1993) *PNAS* 90:4567–4571); In2 gene from maize which responds to benzenesulfonamide herbicide safeners (Hershey et al. (1991) *Mol. Gen. Genetics* 227:229–237 and Gatz et al. (1994) *Mol. Gen. Genetics* 243:32–38); the Adh1 promoter which is inducible by hypoxia or cold stress, the Hsp70 promoter which is inducible by heat stress, and the PPDK promoter which is inducible by light; or Tet repressor from Tn10 (Gatz et al. (1991) *Mol. Gen. Genet.* 227:229–237. A particularly preferred inducible promoter is a promoter that responds to an inducing agent to which plants do not normally respond. An exemplary inducible promoter is the inducible promoter from a steroid hormone gene the transcriptional activity of which is induced by a glucocorticosteroid hormone (Schena et al. (1991) *Proc. Natl. Acad. Sci. U.S.A.* 88:10421).

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

The site-specific recombinase must be expressed in the plant cell in order for mobilization of the viral DNA from the T-DNA. Accordingly, the recombinase protein must be expressed so that it is present in the cell at an effective concentration sometime between when the T-DNA is transferred to the plant cell and before non-integrated T-DNA is lost from the plant cells.

Accordingly, the expression cassette encoding the site-specific recombinase may be supplied on the T-DNA in cis to the viral DNA; in trans on a plant chromosome or extrachromosomal replicon; or may be transferred to the plant near to the time of agro-mediated transformation. The site-specific recombinase gene may be constitutively or transiently expressed, or may be inducible. If cofactors are required for a particular site-specific recombination system, they may be encoded on the T-DNA of the invention or in the plant host chromosomal or extrachromosomal DNA.

By "target site for a site-specific recombinase" is meant a DNA sequence that is recognized by a particular site-specific recombinase. A variety of target sites are known to those skilled in the art and may be used in the methods and compositions of the invention. The site may have the sequence of the cognate site for a given recombinase, or may be modified, so long as it is capable of acting as a target site. The site may be contain the minimal sequences necessary for recombination, or it may contain additional sequences that enhance recombination. Examples of target sites for use in the invention are known in the art and include FRT and loxP sites (See, for example, Schlake and Bode (1994) *Biochemistry* 33:12746–12751; Huang et al. (1991) *Nucleic Acids Research* 19:443–448; Paul D. Sadowski (1995) In Progress in Nucleic Acid Research and Molecular Biology, Vol. 51, pp. 53–91; Michael M. Cox (1989) *In Mobile DNA*, Berg and Howe (eds) American Society of Microbiology, Washington D.C., pp. 116–670; Dixon et al. (1995) 18:449–458; Umlauf and Cox (1988) *The EMBO Journal* 7:1845–1852; Buchholz et al. (1996) *Nucleic Acids Research* 24:3118–3119; Kilby et al. (1993) *Trends Genet.* 9:413–421: Rossant and Geagy (1995) *Nat. Med.* 1: 592–594; Lox Albert et al. (1995) *The Plant J.* 7:649–659: Bayley et al. (1992) *Plant Mol. Biol.* 18:353–361; Odell et al. (1990) *Mol. Gen. Genet.* 223:369–378; and Dale and Ow (1991) *Proc. Natl. Acad. Sci. USA* 88:10558–105620; Qui et al. (1994) *Proc. Natl. Acad. Sci. USA* 91:1706–1710; Stuurman et al. (1996) *Plant Mol. Biol.* 32:901–913; Hartley et al (1980) *Nature* 286: 860–864; Sauer (1994) *Current Opinion in Biotechnology* 5:521–527; and Dale et al. (1990) *Gene* 91:79–85; all of which are herein incorporated by reference.)

Each loxP and FRT site contains two 13 base pair inverted repeats which flank an 8 base pair spacer. The FRT site contains an additional non-essential 13 base pair repeat. The sequences of the loxP and FRT sites are shown in FIG. 1. A minimal FRT site (SEQ ID NO:3) comprising two 13 base pair repeats, separated by an 8 base spacer, is:

5'-GAAGTTCCTATTC[TCTAGAAA]
   GTATAGGAACTTC3' wherein the nucleotides within the brackets indicate the spacer region. The nucleotides in the spacer region can be replaced with a combination of nucleotides, so long as the two 13-base repeats are separated by eight nucleotides. FLP is a conservative, site-specific recombinase, capable of catalyzing inversion of a nucleic acid sequence positioned between two inversely oriented FRTs; recombination between two molecules each containing a FRT site; and excision between FRT sites. The core region is not symmetrical, and its asymmetry dictates the directionality of the reaction. Recombination between inverted FRT sites causes inversion of a DNA sequence between them, whereas recombination between directly oriented sites leads to excision of the DNA between them.

T-DNAs containing viral DNA flanked by recombinations sites, expression cassettes for site-specific recombinases and vectors carrying these sequences may be constructed using standard molecular biology techniques. See, for example, Sambrook et al. (eds.) *Molecular Cloning: A Laboratory Manual*, Second Edition, (Cold Spring Harbor Laboratory Press, cold Spring Harbor, N.Y. 1989).

Typical vectors useful in the methods and compositions of the invention are well known in the art and include vectors derived from the tumor-inducing (Ti) plasmid of *Agrobacterium tumefaciens* described by Rogers et al, (1987) *Meth. in Enzymol.*, 153:253–277. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., *Gene*, 61:1–11 (1987) and Berger et al., *Proc. Natl. Acad. Sci. U.S.A.*, 86:8402–8406 (1989). Another useful vector herein is plasmid pBI101.2 that is available from Clontech Laboratories, Inc. (Palo Alto, Calif.).

Techniques for transforming a wide variety of higher plant species are well known and described in the technical, scientific, and patent literature. See, for example, Weising et al., *Ann. Rev. Genet.* 22: 421–477 (1988). These methods are useful for transforming a plant cell with a site-specific recombinase expression cassette. This step will be necessary if the cassette is not included in the transferred T-DNA. The expression cassette encoding the site-specific recombinase may be present in the plant genome prior to Agroinfection or may be transformed into the plant around the time of transfer of the T-DNA to the plant cell so that it will be transiently expressed. For example, the DNA construct may be introduced directly into the genomic DNA of the plant cell using techniques such as electroporation, PEG poration, particle bombardment, silicon fiber delivery, microinjection of plant cell protoplasts or embryogenic callus, or *Agrobacterium*-mediated transformation (Hiei et al. (1994) *Plant J.* 6:271–282).

The introduction of DNA constructs using polyethylene glycol precipitation is described in Paszkowski et al., *Embo J.* 3: 2717–2722 (1984). Electroporation techniques are described in Fromm et al., *Proc. Natl. Acad. Sci.* 82: 5824 (1985). Ballistic transformation techniques are described in Klein et al., *Nature* 327: 70–73 (1987).

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo 1986*, Butterworth, Stoneham, Mass., pp. 27–54 (1986). A variety of plant viruses that can be employed as vectors are known in the art and include cauliflower mosaic virus (CaMV), geminivirus, brome mosaic virus, and tobacco mosaic virus.

Plants cells stably transformed with a site-specific recombinase expression cassette can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, MacMillan Publishing Company, New York, pp. 124–176 (1983); and Binding, *Regeneration of Plants, Plant Protoplasts*, CRC Press, Boca Raton, pp. 21–73 (1985).

The regeneration of plants containing the recombinase gene introduced by *Agrobacterium* from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. U.S.A.*, 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement*, 3$^{rd}$ edition, Sprague and Dudley Eds., American Society of Agronomy, Madison, Wis. (1988).

One of skill will recognize that after the site-specific recombinase expression cassette is stably incorporated in transgenic plants and confirmed to be operable, it can be introduced into other plants by sexual crossing. Any of a number of standard breeding techniques can be used, depending upon the species to be crossed.

The methods and compositions of the invention are useful to mobilize viral DNA from T-DNAs transferred by agroinfection to any plant host. As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to *Agrobacterium* transformation techniques, including both monocotyledonous and dicotyledonous plants. A particularly preferred monocot is maize. Other monocots of particular interest include wheat, rice, barley, sorghum and rye. Dicots of particular interest include soybean, *Brassica*, sunflower, alfalfa, and safflower.

The T-DNA containing the viral DNA flanked by sites for a site-specific recombinase is transferred to a plant cell by agroinfection. *Agrobacterium tumefaciens*-meditated transformation techniques are well described in the scientific literature. See, for example Horsch et al. *Science* 233: 496–498 (1984), Fraley et al. *Proc. Natl. Acad. Sci.* 80: 4803 (1983); and Kado (1991) *Crit. Rev. Plant Sci.* 10:1. Descriptions of the *Agrobacterium* vector systems and methods for *Agrobacterium*-mediated gene transfer are provide in Gruber et al., supra; Miki, et al, supra; and Moloney et al. (1989) *Plant Cell Reports* 8:238. Although *Agrobacterium* is useful primarily in dicots, certain monocots can be transformed by *Agrobacterium*. For instance, *Agrobacterium* transformation of maize is described in U.S. Pat. No. 5,550,318. Other methods of agroinfection include *Agrobacterium rhizogenes*-mediated transformation (see, e.g., Lichtenstein and Fuller In: *Genetic Engineering*, Vol. 6, PWJ Rigby, Ed., London, Academic Press, 1987; and Lichtenstein, C. P., and Draper, J, In: *DNA Cloning*, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16.

Optimized methods and vectors for *Agrobacterium*-mediated transformation of plants in the family Graminae, such as rice and maize have been described by Heath et al. (1997) *Mol. Plant-Microbe Interact.* 10:221–227; Hiei et al. (1994) *Plant J.* 6:271–282 and Ishida et al. (1996) *Nat. Biotech.* 14:745–750, the contents of which are incorporated herein by reference. The efficiency of maize transformation is affected by a variety of factors including the types and stages of tissue infected, the concentration of *Agrobacterium*, the tissue culture media, the Ti vectors and the maize genotype. Super binary vectors carrying the vir genes of *Agrobacterium* strains A281 and A348 are useful for high efficiency transformation of monocots. However, even without the use of high efficiency vectors, it has been demonstrated that T-DNA is transferred to maize at an efficiency that results in systemic infection by viruses introduced by agroinfection, although tumors are not formed (Grimsley et al. (1989) *Mol. Gen. Genet.* 217:309–316, the contents of which are incorporated herein by reference). This is because integration of the T-DNA containing the viral genome is not required for viral multiplication, since the excised viral genome acts as an independent replicon.

Another useful basic transformation protocol involves a combination of wounding by particle bombardment, followed by use of *Agrobacterium* for DNA delivery, as described by Bidney et al. (1992) *Plant Mol. Biol.* 18:301–313. In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with *Agrobacterium*. To start the co-cultivation for intact meristems, *Agrobacterium* is placed on the meristem. After about a 3-day co-cultivation period the meristems are transferred to culture medium with selection agents.

The split meristem method involves imbibing seed, breaking of the cotyledons to produce a clean fracture at the plane of the embryonic axis, excising the root tip and then bisecting the explants longitudinally between the primordial leaves. The two halves are placed cut surface up on the medium then bombarded twice with particles, followed by co-cultivation with *Agrobacterium*. For split meristems, after bombardment, the meristems are placed in an *Agrobacterium* suspension for 30 minutes. They are then removed from the suspension onto solid culture medium for three day co-cultivation. After this period, the meristems are transferred to fresh medium with cefotaxime (plus selection agents).

The excision of viral DNA from the T-DNA may be determined by a variety of means including but not limited to observation of viral lesions or other signs of viral infection on the plant, by antibody-based detection of viral proteins, by amplification of PCR products specific to a circular genome, or by Northern analysis for viral RNA. In addition, assays for FLP recombinase activity are known and generally measure the overall activity of the enzyme on DNA substrates containing FRT sites. In this manner, a frequency of excision of the sequence can be determined. Excision of DNA from a linear molecule or intermolecular recombination frequency induced by the enzyme may be assayed, as described, for example, in Babineau et al. (1985) *JBC* 260:12313; Meyer-Leon et al. (1987) *NA Res* 15:6469; and Gronostajski et al. (1985) *JBC* 260:12328.

The following examples are offered by way of illustration not by way of limitation.

EXPERIMENTAL

Example 1

Construction of T-DNA Vectors Containing Viral DNA Flanked by Site-Specific Recombination Sites DNA fragments containing viral DNA flanked by FRT or loxP site-specific recombination sites are constructed either by synthesizing, annealing and ligating complementary oligonucleotides or by creating primers for PCR amplification of a DNA product containing the FRT or loxP site and restriction sites useful for cloning into T-DNA near the 5' end of the PCR product.

Figure 5:
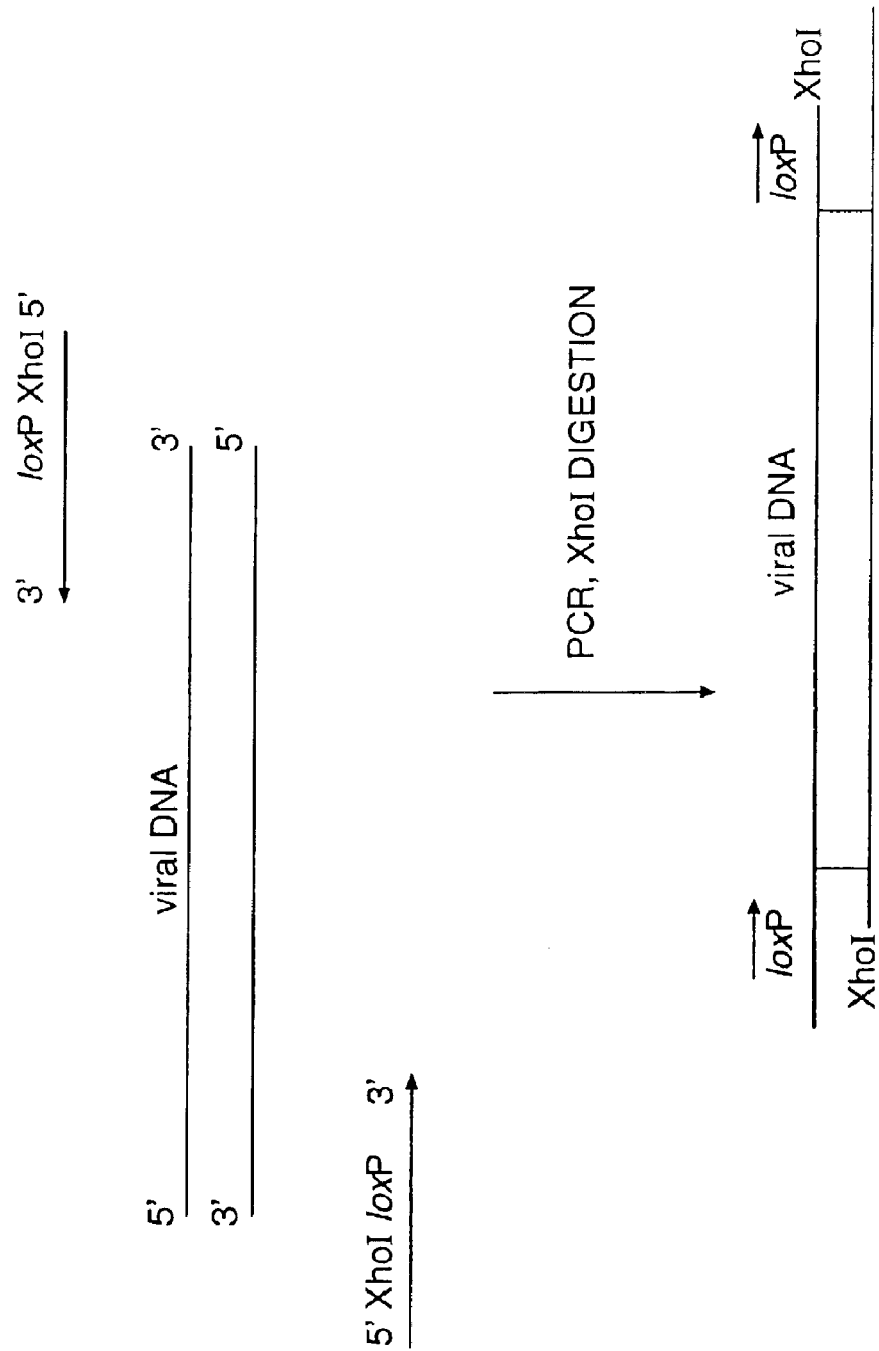
FIG. 5 schematically illustrates a PCR protocol for construction of a viral DNA flanked by loxP target sites and XhoI restriction sites.

For example, long PCR primers may be designed wherein the 3' end of the primer hybridizes to the 5' end of the viral genome of interest and the 5' end of the primer further contains a loxP site and useful cloning sites (see FIG. 5). The resulting PCR product is digested with the appropriate restriction enzyme and inserted into the T-DNA of an *Agrobacterium* binary vector as described by Bevan, M. (1984) *Nucl. Acids Res.* 12:8711–8721; herein incorporated by reference. An expression cassette for Cre is also inserted into the T-DNA. The resulting constructs are transformed into *E. coli*, screened, and then transferred to *Agrobacterium*.

Example 2

Transfer of T-DNA to Dicotyledonous Plant Cells

*Nicotiana tabacum* BY-2 cells are propagated in Murashige and Skoog medium (Gibco BRL) containing 3% sucrose, 1 μg/ml thiamine, 0.2 μg/ml 2,4-D, and 370 μg/ml $KH_2PO_4$. *Zea mays* Black Mexican Sweet (BMS) cells are propagated in Murashige and Skoog medium containing 2% sucrose, 2 μg/ml 2,4-D, 0.2 mg/ml myoinositol, 0.13 mg/ml L-asparagine, 0.13 μg/ml nicotinic acid, and 0.25 μg/ml each of thiamine, pyridoxine, and pantothenic acid. The cultures are shaken at 140 rpm at 25° in continuous light.

To infect plant cells, virulence (vir) gene activity is induced by treatment with acetosyringone in *Agrobacterium* carrying the vector constructed in Example 1. *Agrobacterium* cells are grown to a density of $2 \times 10^9$ cells per ml (A=100, using a Klett-Summerson spectrophotometer, red filter) in AB-sucrose medium. The cells are centrifuged at 10,000g, suspended at a concentration of $1 \times 10^9$ cells per ml (A=50) in induction medium (AB salts, 0.5% glucose, 2 mM sodium phosphate, 50 Mm Mes, Ph 5.6, 50 μM acetosyringone), and incubated with gentle shaking at 25° for 14 to 18 hr. After washing the bacterial cells in plant culture medium, plant cells are inoculated with induced *Agrobacterium* (~20 bacterial cells per plant cell, except where noted otherwise) and cocultivated at 25° with shaking at 140 rpm for various periods of time. Most of the bacteria is washed off by centrifugation of the cocultivation mixture at 300 rpm (model GLC-2 clinical centrifuge; Beckman Sorvall, Newtown, Conn.) for 2 min. The plant cell pellet is suspended and washed once more in plant culture medium and then resuspended in culture containing either 100 μg/ml timentin or 200 μg/mL cefotaxime. Mobilization of viral genomes from the T-DNA is monitored by quantitating infectious viral particles.

Example 3

Transfer of T-DNA to Monocotyledonous Plants

Prior to inoculation, strains of *Agrobacterium* carrying the vector constructed in Example 1 are streaked out on YEB (Grimsley et al.(1986) *Proc. Natl. Acad. Sci. USA*, 83:3282–3286) plates solidified with 1.5% agar and supplemented with 100 μg/ml rifampicin and 25 μg/ml kanamycin and allowed to grow for 48 h. A single colony is used to inoculate 10 ml of liquid YEB medium in a 100 ml Erlenmeyer flask supplemented with antibiotics as previously. Growth is continued with shaking at 200 r.p.m. for 24 h, then 500 μl of this culture is used to inoculate a similar flask and growth continued for a further 20 h. This procedure yields a final density of viable *Agrobacterium* cells in the region of $10^9$/ml (estimated by plating). The cells are then harvested by centrifugation and resuspended in an equal volume of 10 mM $MgSO_4$ without antibiotics; such a suspension is subsequently referred to as undiluted or 10° dilution; for experiments involving a dilution series 10 mM $MgSO_4$ was also used as the diluent.

Maize seeds for 10-day old plants are sown in pots in a phytotron in a 12 hour light/dark cycle at 25° in a light intensity of about 10000 lux (Sylvania 215 W fluorescent lamps type F96T12/CW/VHO) then moved to the BL3 containment laboratory immediately prior to inoculation; subsequent growth conditions have been described (Grimsley et al.(1987) *Nature* 325:177–179). Three-day old seedlings are prepared by (i) sterilization by stirring for 20 min in 0.7% calcium hypochlorite solution, (ii) washing three times (stirring for 20 min each time) in sterile distilled water (iii) preparing 9 cm diameter presterilized Petri dishes with 3 sheets of sterile 8.5 cm diameter Macherey-Nagel (Germany) filter paper in the bottom and ca. 10 ml of sterile water per dish, (iv) putting ca. 20 seeds into each geranium dish, and (v) incubating in the dark at 28° for 3 days, or until the distance between the scutellar node and the apical tip of the coleoptiles is 1–2 cm.

For inoculation of plants, a 50 μl or a 100 μl Hamilton syringe fitted with a 0.4 mm diameter disposable needle is loaded with the bacterial suspension avoiding trapped air bubbles. Between inoculations with different bacterial strains the needle is discarded and the syringe flushed out 3 times with 100% ethanol and 3 times with sterile distilled water. 10-day old plants are inoculated by (i) abrasion of an upper leaf, applying 20 μl of suspension, and rubbing in with carborundum powder until the leaf appears wet all over, (ii) injection of 10 μl of bacterial suspension into the central part of the plant either just above the first leaf blade, or 1 cm below the first leaf blade, or at the base of the plant, in the meristematic region where adventitious roots later begin to appear. Three-day old seedlings are injected with 10 µl of bacterial suspension in different ways by (i) pushing the needle down through the apical tip of the coleoptile to the coleoptilar node, (ii) injecting 2 mm below the apical tip of the coleoptile, (iii) 2 mm above the coleoptilar node, (iv) at the coleoptilar node, (iv) 2 mm below the coleoptilar node, (v) at the scutellar node, and by pushing the needle up through the primary root to a region close to the scutellar node. Ten µl is used as a standard inoculum of bacterial suspension, but only 1–2 µl routinely remains in the inoculation site, the rest is forced out, usually coming out from the point of entry of the inoculating needle. Following inoculation seedlings are planted immediately in damp soil, incubated as before (Grimsley et al.(1987) Nature 325:177–179), and observed daily for the appearance of symptoms of viral infection, characterized by the appearance of yellow spots and/or stripes at the base of new leaves.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for expressing a nucleotide sequence of interest in a plant cell comprising,
   a) providing an *Agrobacterium* replicon having a T-DNA, wherein said T-DNA comprises in a 5' to 3' or a 3' to 5' orientation, a first target site for a site-specific recombinase, a viral replicon, said nucleotide sequence of interest operably linked to a first promoter that drives expression in said plant cell, and a second target site for said site-specific recombinase, wherein said first and said second target site are directly repeated and identical with respect to one another;
   b) infecting said plant cell with an *Agrobacterium* carrying said *Agrobacterium* replicon under conditions that allow transfer of said T-DNA and expression of said site-specific recombinase in said plant cell; and,
   wherein said plant cell, said T-DNA, or said viral replicon comprises a nucleotide sequence encoding said site-specific recombinase, an active fragment of said site-specific recombinase, or an active variant of said site-specific recombinase, wherein said nucleotide sequence is operably linked to a second promoter that drives expression in said plant cell, and wherein said active fragment or said active variant of said site-specific recombinase retains the ability to catalyze a recombination event.

2. The method of claim 1, wherein said site-specific recombinase is a member at the integrase family.

3. The method of claim 2, wherein said site-specific recombinase comprises FLP, Cre, Int, SSVI, Integrase R, or an active fragment or an active variant thereof.

4. The method of claim 3, wherein said first and said second target sites are selected from the group consisting of a FRT site and a mutant FRT site.

5. The method of claim 4, wherein said mutant FRT site is FRT5 (SEQ ID) NO: 4), FRT6 (SEQ ID NO: 5) or FRT7 (SEQ ID NO: 6).

6. The method of claim 4, wherein said site-specific recombinase comprises an active variant of FLP.

7. The method of claim 4, wherein said site-specific recombinase comprises FLP.

8. The method of claim 4, wherein said site-specific recombinase comprises moFLP.

9. The method of claim 4, wherein said site-specific recombinase comprises an active fragment of FLP.

10. The method of claim 3, wherein said first and said second target sites are selected from the group consisting of a LOX site or a mutant LOX site.

11. The method of claim 10, wherein said site-specific recombinase comprises an active variant of Cre.

12. The method of claim 10, wherein said site-specific recombinase comprises Cre.

13. The method of claim 10, wherein said site-specific recombinase comprises moCre.

14. The method of claim 10, wherein said site-specific recombinase comprises an active fragment of Cre.

15. The method of claim 1, wherein said plant coil is from a monocot.

16. The method of claim 15, wherein said monocot is maize, wheat, rice, barley, sorghum, or rye.

17. The method of claim 16, wherein said monocot is maize.

18. The method of claim 1, wherein said plant cell is from a dicot.

19. The method of claim 18, wherein said dicot is soybean, canola, *Brassica*, sunflower, alfalfa, or safflower.

20. A plant cell having a DNA construct comprising in a 5' to 3' or a 3' to 5' orientation a first target site for a first site-specific recombinase, a viral replicon, and a second target site for said first site-specific recombinase, wherein said first and said second target site are directly repeated and identical with respect to each other.

21. The plant cell of claim 20, wherein said DNA construct is stably incorporated into the genome of said plant cell.

22. The plant cell of claim 20, wherein said DNA construct comprises in a 5' to 3' or a 3' to 5' orientation said first target site for said first site-specific recombinase, said viral replicon, a nucleotide sequence of interest, and said second target site for said first site-specific recombinase.

23. Tho plant cell of claim 22, wherein said DNA construct is stably incorporated into the genome of said plant cell.

24. The plant of cell claim 23, wherein said nucleotide sequence of interest is operably linked to a promoter that drives expression in said plant cell.

25. The plant cell of claim 20 wherein said DNA construct is contained within a T-DNA.

26. The plant cell of claim 20, wherein said DNA construct further comprises a nucleotide sequence encoding said first site-specific recombinase.

27. The plant cell of 20, claim said plant cell comprises a nucleotide sequence encoding said first site-specific recombinase.

28. The plant cell of claim 27, wherein said first site-specific recombinase is a member of the integrase family.

29. The plant cell of claim 28, wherein said first site-specific recombinase is FLP, Cre, Int, SSVI, lntegrase R, or an active fragment or an active variant thereof.

30. The plant cell of claim 20, wherein said first and said second target site is an FRT site, a mutant FRT site, a LOX site, or a mutant LOX site.

31. The plant cell of claim 20, wherein said viral replicon is a MSV replicon, a WDV replicon, a TGMV replicon, or a TMV replicon.

32. The plant cell of claim 20, wherein said plant cell is from a monocot.

33. The plant cell of claim 32, wherein said monocot is maize, wheat, rice, barley, sorghum, or rye.

34. The plant cell of claim 33, wherein said monocot is maize.

35. The plant cell of claim 20, wherein said plant cell is from a dicot.

36. The plant cell of claim 35, wherein said dicot is soybean, canola, *Brassica*, sunflower, alfalfa, or safflower.

37. The plant cell or claim 20, wherein said plant cell is in a plant.

38. The plant cell of claim 21, wherein said plant cell is in a plant.

39. The plant cell of claim 21, wherein said plant cell is in a seed.

40. The plant cell of claim 22, wherein said DNA construct comprises in the 5' to 3' or the 3' to 5' orientation the first target site for said first site-specific recombinase, said viral replicon, a third target site for a second site-specific recombinase, the nucleotide sequence of interest, and the second target site for said first site-specific recombinase, wherein said first and said second target site are directly repeated and identical with respect to each other, and said third target site is non-identical to said first and said second target site.

41. The method of claim 1, wherein said *Agrobacterium* replicon comprises a Ti plasmid or a Ri plasmid.

42. The method of claim 1, wherein said viral replicon is a MSV replicon, a WDV replicon, a TGMV replicon, or a TMV replicon.

43. The method of claim 1, wherein said second promoter is art inducible promoter.

44. The method of claim 1, wherein said plant cell is in a plant.

45. The plant cell of claim 40, wherein said DNA construct is stably incorporated into the genome of said plant cell.

46. The plant cell of claim 40, wherein said DNA construct is contained within a T-DNA.

47. The plant cell of claim 40, wherein said first and said second site-specific recombinase are identical.

48. The plant cell of claim 40, wherein said first or said second site-specific recombinase is FLP, Cre, Int, SSVI, or Integrase R, or an active fragment, or an active variant thereof.

49. The plant cell of claim 40, wherein said first, said second, or said third target sites are selected from the group consisting of a FRT site, a mutant FRT site, a LOX site, and a mutant LOX site.

50. The plant cell of claim 49, wherein said first or said second site-specific recombinase comprises FLP.

51. The plant cell of claim 49, wherein said mutant FRT site is a FRT5 site (SEQ ID NO:4), a FRT 6 site (SEQ ID NO:5), or a FRT 7 site (SEQ ID NO:6).

52. The plant cell of claim 49, wherein said first or said second site-specific recombinase comprises Cre.

53. The plant cell of claim 40, wherein said nucleotide sequence of interest is operably linked to a promoter that drives expression in said plant cell.

54. The plant cell of claim 40, wherein said DNA construct further comprises a nucleotide sequence encoding said first or said second site-specific recombinase.

55. The plant cell of claim 40, wherein said viral replicon is a MSV replicon, a WDV replicon, a TGMV replicon, or a TMV replicon.

56. The plant cell of claim 40, wherein said plant cell is from a monocot.

57. The plant cell of claim 56, wherein said monocot is maize, wheat, rice, barley, sorghum, or rye.

58. The plant cell or claim 57, wherein said monocot is maize.

59. The plant cell of claim 40, wherein said plant cell is from a dicot.

60. The plant cell of claim 59, wherein said dicot is soybean, canola, *Brassica*, sunflower, alfalfa or safflower.

61. The plant cell of claim 40, wherein said plant cell is in a plant.

62. The plant cell of claim 40, wherein said plant cell is in a seed.

* * * * *